United States Patent [19]

Leach

[11] 4,010,739
[45] Mar. 8, 1977

[54] SPHYGMOMANOMETER

[76] Inventor: John Meredith Leach, Box 341, Port Jefferson, N.Y. 11777

[22] Filed: Nov. 3, 1975

[21] Appl. No.: 628,227

[52] U.S. Cl. .............................. 128/2.05 G; 73/411
[51] Int. Cl.[2] ........................................ A61B 5/02
[58] Field of Search ............... 128/2.05 G, 2.05 P; 73/411

[56] References Cited

UNITED STATES PATENTS

| | | | |
|---|---|---|---|
| 1,282,632 | 10/1918 | Roesch | 128/2.05 G |
| 1,848,489 | 3/1932 | Motherwell | 128/2.05 |
| 3,056,401 | 10/1962 | Greenspan et al. | 128/2.05 G |
| 3,542,011 | 11/1970 | Langenbeck | 128/2.05 G |

FOREIGN PATENTS OR APPLICATIONS

| | | | |
|---|---|---|---|
| 202,696 | 9/1958 | Austria | 128/2.05 G |
| 772,284 | 8/1934 | France | 128/2.05 G |
| 43,821 | 6/1934 | France | 128/2.05 G |
| 1,282,926 | 12/1961 | France | 128/2.05 G |

*Primary Examiner*—Kyle L. Howell

[57] ABSTRACT

A sphygmomanometer in which the gauge in addition to indicating the extent of the systolic and diastolic pressures also indicates when these pressures occur directly adjacent the gauge pressure hand without the use of any stethoscope or electronic medium.

2 Claims, 4 Drawing Figures

SPHYGMOMANOMETER

BACKGROUND OF THE INVENTION

The blood pressure equipment now available requires either the use of a stethoscope of an electronic system involving a sensor, circuitry, visual or audible signal or both and a power source such as batteries. The stethoscope is a separate instrument which must be available, it is awkward to use, gives variable results between different operators depending on their hearing abilities and is expensive. The electronic system requires a separate container for the electrical components which makes it awkward to use, is always subject to power failure at critical times and is very expensive. The closest prior art developed relating to the present invention discloses a pulse indicator utilizing a separate bladder for the body contact equipment which is connected to a water gauge carried by the pressure gauge. The water gauge utilizes an air bubble located in the water column which is supposed to pulsate when the heart beats are picked up by the separate bladder. If the bubble does so pulsate is doubtful because the low energy heart beats have to force the water column against an elastic cap sufficiently to expand the cap. This would most probably require more energy than can be supplied by a heart beat. Also, the bubble would invariably migrate to the end of the tube where it would be difficult to see it move, and any movement of the bubble wherever it might be would be so slight as to make it very difficult to detect.

SUMMARY OF THE INVENTION

The present invention is an improvement on the conventional sphygmomanometer and more specifically on the blood pressure indicating gauge thereof. The improvement on the gauge enables this single instrument to measure and indicate the blood pressure and also indicate the occurrence of the systolic and diastolic pressure points, both very clearly and easily. Thereby completely eliminating the need for any stethoscope or electronic detector of the high and low pressures. This makes the improved equipment of the present invention easier and more convenient to use, more accurate and much more economical than the presently available equipment. All of this is accomplished by the addition of one pointer hand and two simple pivots to a conventional type of gauge which makes for a very simple and efficient blood pressure determinator. It is an object of the present invention to provide a sphygmomanometer which utilizes only a single instrument besides the body contact equipment as a blood pressure determinator. It is a further object of the present invention to provide a single instrument in which the occurrence of the two significant blood pressures and the extent of the blood pressure at each occurrence can be read in the same very small field of vision very accurately and very easily and conveniently. Other objects and advantages of the present invention will become apparent to those skilled in the art upon recourse to the following specification and claims.

BRIEF DESCRIPTION OF THE DRAWINGS

The now preferred embodiment of the present invention is disclosed in the accompanying drawing which is to be considered as descriptive and not limitative as many changes and modifications can be made in the structural details without departing from the spirit of the invention. In the drawing.

DETAILED DESCRIPTION

Figure 3:
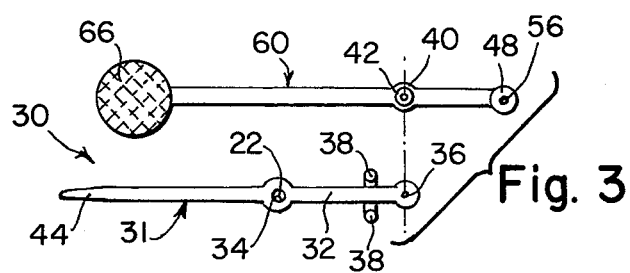
FIG. 3 is a is a horizontally expanded view of the components shown in FIG. 2.
Figure 2:
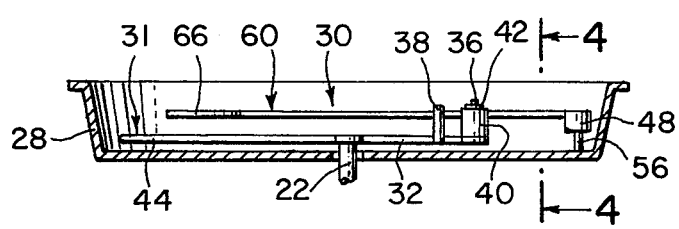
FIG. 2 is a side view of the indicating and motion amplifying components of the present invention.
Figure 4:
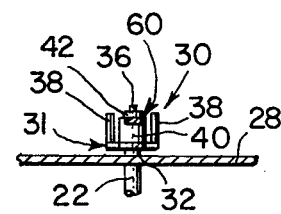
FIG. 4 is a cross sectional view taken substantially on the plane indicated by line 4 – 4 of FIG. 2 and looking in the direction of the arrows.
Figure 1:
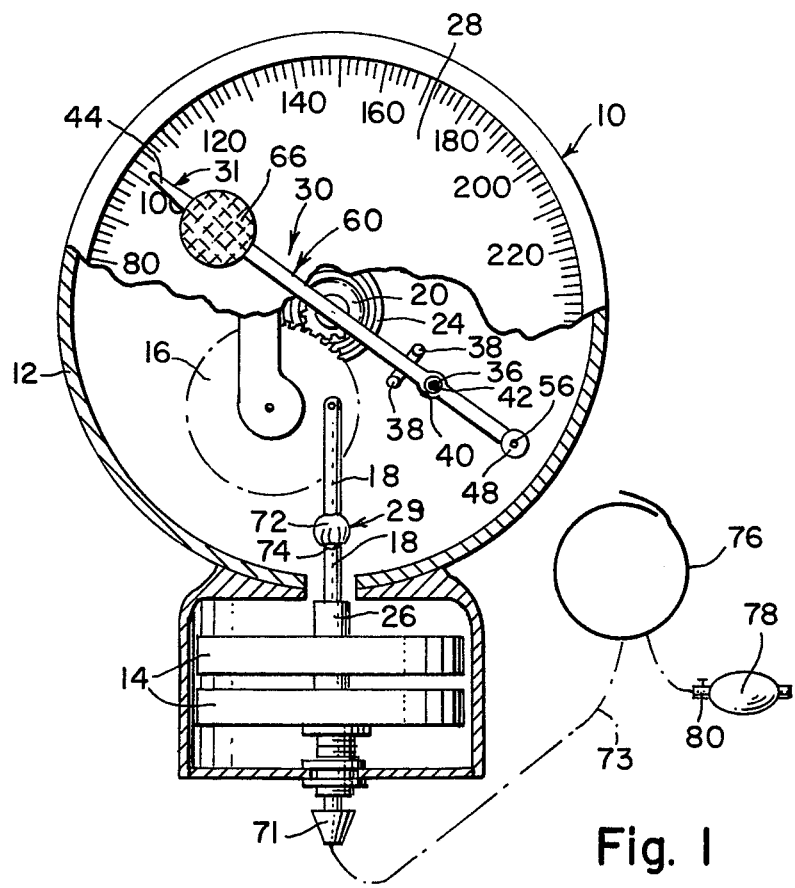
FIG. 1 is a face view of a gauge provided with the features of the present invention with a part of the calibrated dial removed to show the inner mechanism.

The gauge used can be any type of pressure gauge although what is usually used and seems to be the best suited for a sphygmomanometer is an aneroid bellows type as shown at 10 in FIG. 1. It comprises an outer casing 12 which houses an aneroid bellows 14 and a gear 16 which is connected to the bellows by a rod 18. The gear 16 drives a smaller gear 20 rigidly mounted on the main shaft 22. A main spring 24 also connected to the main shaft biases the main shaft in a direction to cause the gear 16 to rotate in a direction to keep the lower end of the rod 18 in tight contact with the hollow hub 26 on the bellows 14. A pointer hand is normally carried by the outer end of the main shaft 22 but is omitted in this application. A properly calibrated dial 28 normally coacts with the pointer hand to indicate the blood pressure. Since the gauge thus far is conventional common expedients such as shaft bearings, limit stop, bezel ring and crystal cover have been omitted for the purpose of clarification. About the only required specification for the pressure gauge is that it must be sufficiently sensitive to reflect heart beats as at least minor oscillations or pulsations of the pointer hand. This does not involve unusual or expensive construction. The sensitivity of a gauge can be increased by omitting the spring 24 and anchoring the rod 18 to the hub 26 by any suitable means such as threading the lower end and screwing it into a suitably tapped hole in the bottom of the hollow tub 26 (not shown). When this is done it is very helpful to form the rod 18 in two sections and connect them by a well know quick release type of ball and socket flexible joint 29. This significantly aids oriented assembly and calibration, later adjustment and also permits the rod 18 to flex as required by the rotation of gear 16. This positive connection of the pod 18 and the bellows relieves the bellows of the pressure of the spring 24 because the bellows resilience serves to return the gears, shaft, rod and pointer hand to zero position and thereby makes the spring non-essential but optional. The features which contribute to the utility of the present invention in dispensing with the need to use a stethoscope to obtain a blood pressure reading comprise the assembly 30 which includes two elements as shown in the horizontally expanded view FIG. 3. These elements are a combination hand 31 having a pointer end 44 and an indicator drive end 32. 31 is provided with an opening 34 which is force fitted over the upper end of the main drive shaft 22 and an upstanding pin 36 on the drive end. Hand 31 is also provided with two upstanding indicator stop pins 38. The second element is an indicator arm 60 provided with a hub 40 having a through opening forming a loose fit on the pin 36 and held in place on the pin by a small split ring 42. A small counterweight 48 is suitably attached to the short end of the indicator arm 60 to balance the weight of the longer end of the arm and is provided with a small opening in which is suitably cemented a small fiber pivot point 56 made of any desired natural or synthetic material. A disc 66 is suitably attached to the opposite end of arm 60 and painted a bright color such as orange to be exceptionally visible. From FIGS. 2 and 3 it can be seen that the two pins 38 act as stops to limit the relative angular movement of the drive end 32 and the indicator arm 60 so that indicator arm 60 is generally moved with the drive end 32 but limited movement between the two is permitted by the spacing between the two pins 38. The flexible connector 29 which is used when no spring 24 is used comprises a socket formed of spring fingers 72 connected to one section of the rod 18 and a ball 74 connected to the other section of the rod 18. This permits relative angular movement of the rod sections but no relative linear movement and the ball can be moved into and out of the socket by applying sufficient pressure to flex and open the fingers. The gauge 10 is provided with a bellows connection 71 which is connected by the usual rubber tube schematically shown at 73 to a conventional arm cuff 76 or other live body contact blood pressure sensitive equipment. Such equipment is usually inflated by a suitable pump or a simple squeeze bulb 78 having a pressure release valve 80 or any other desired source of pressure. Cuffs, squeeze bulbs, etc. are well disclosed in the "Baumanometer - Blood Pressure and Accessories" Catalog, published in 1972 by the A. A. Baum Co., Inc., Copiague, N. Y. 11726. Any other desired type of blood pressure sensitive equipment can be used as long as it has an indicating gauge with a pointer. In using this invention, the cuff 76 or other body contact equipment is applied to the body of the person whose blood pressure is to be determined; usually by applying the cuff 76 to an upper arm area, the pressure valve 80 is closed and the bulb is squeezed to apply pressure by inflating the cuff until the blood pressure registered by the hand 44 on the calibrated dial 28 is above what the systolic (high) pressure of the person is expected to be and further inflation is stopped. If the indicator head 66 is still oscillating, continue the inflation until the indicator head stops oscillating. Then gradually release the pressure through release valve 80 until the indicator head 66 starts oscillating and read the pressure registered by the hand 44 on the calibrated dial 28 at that exact point, which is easy because the indicator head 66 and the indicator hand 44 are in the same field of vision. This is the systolic (high) pressure. Continue gradually releasing the pressure through valve 80 until the indicator head 66 stops oscillating and read the pressure registered by the hand 44 on the calibrated dial 28 exactly at that point. This is the diastalic (low) pressure of the person. If desired the pressure release valve 80 may be released at short intervals instead of continuously. The function of the invention which took place during the above blood pressure determination was as follows: When air pressure started to increase within the bellows 14 when the bulb 78 was squeezed the bellows started to expand which moved the rod 18 so as to turn the gear 16 which turned the gear 20 and the main shaft 22 fastened to the gear 20 which moved the drive lever 32 which is part of the first hand 31. Assuming that the lever 32 was at the position shown in FIG. 4 at the start of its movement, which would have been clockwise as viewed in FIG. 1, because of its connection with indicator arm 60 through the pivot pin 36 it would have first moved indicator arm 60 slightly counterclockwise with the indicator arm 60 pivoting on the pivot point 56 which was retarded from movement at that time because of the slight friction between the pivot point 56 and the dial surface 28 until the lever 32 contacted the stop 38 when the friction between pivot point 56 and the surface of dial 28 was overcome and the lever 32 and indicator arm 60 then moved clockwise together until the increasing pressure stopped. When the pressure was decreased the exact reversal of the parts movements occurred. It is generally accepted dogma that the heart beat is sufficiently effective on the blood pressure between the systolic and distolic pressures as to be audible through a stethoscope. Between these two pressures each heart beat also produces a slight pulsation in the blood pressure which is reflected as a very slight pulsation on a gauge pointer such as the first hand 31 and its short lever 32 but these pulsations are not very distinct to the naked eye. During the period when the pressure was being released in the above blood pressure determination slight pulsating motions of the lever 32 were greatly amplified by the motion amplifying means comprising short lever 32, pivot 36, pivot 56 and long indicator arm 60 with the result that the movements of indicator head 66 were very visible and distinct to indicate when to read the position of pointer 44 right next to the indicator head 66 on the calibrated dial 28. Because the pulsations are slight and weak in intensity it is necessary that all components of the motion amplifying means be made of the lightest materials and of the smallest sizes as is consistent with the low strength required. The pivot point 56 forms a pivotal mounting for the indicator arm 60 when the pivot point 56 is not moving. It is to be understood that the spring 24 and the rod with joint 29 to make it flexible may both be used at the same time if desired. The gauge of the present invention may be attached to the body contact equipment for support, hung on the wall with an enlarged dial for distant reading or supported in any other way or position desired. The foregoing is to be considered as descriptive and not limitative as many changes and modifications can be made therein without departing from the concept of the invention.

The invention having been described, what is claimed is:

1. In a gauge of the type used in blood pressure determinators, a main shaft for said gauge mounted for rotation therein, means for rotating said shaft in accordance with variations in the blood pressure of a given subject, a first hand mounted on said shaft for rotation therewith, a calibrated dial over which said first hand moves, a pivot mounted on said first hand at a point removed from said mounting of said first hand on said main shaft for movement with said first hand, a second hand mounted for rotation on said pivot, a second pivotal mounting for said second hand carried thereby at a point removed from said pivot and in contact with said dial, stop arms carried by said first hand in position to permit limited movement of said second hand separate from movement of said first hand at which time said second hand pivots on said pivot carried by said second hand which is at that time in stationary contact with said dial, said stop arms being in position to contact said second hand at the end of its limited movement and move said second hand with said first hand at which time said pivot carried by said second hand slides over said dial in contact therewith.

2. In a gauge of the type used in blood pressure determinators, a main shaft for said gauge mounted for rotation thereon, means for rotating said main shaft in accordance with variations in the blood pressure of a given subject, a first hand mounted for rotational movement with said main shaft, a calibrated dial over which said first hand moves, a pivot mounted on said first hand at a point removed from said mounting of said first hand on said main shaft for rotation with said first hand, and a second hand mounted for rotation on said pivot.

* * * * *